United States Patent [19]

Auck et al.

[11] Patent Number: 5,950,642
[45] Date of Patent: Sep. 14, 1999

[54] CLEAN CONNECTION AND SAMPLING APPARATUS AND METHOD

[75] Inventors: Rodney D. Auck, Austin; Kenneth Kisamore, Elgin, both of Tex.

[73] Assignee: Porter Company/Mechanical Contractors, Manchaca, Tex.

[21] Appl. No.: 08/969,149

[22] Filed: Nov. 12, 1997

[51] Int. Cl.[6] ........................................ B08B 9/00
[52] U.S. Cl. ................ 134/22.1; 134/22.18; 134/102.2; 134/113; 134/200
[58] Field of Search ................ 134/22.1, 22.12, 134/22.18, 102.1, 102.2, 198, 200, 104.4, 113

[56] References Cited

U.S. PATENT DOCUMENTS

| | | | |
|---|---|---|---|
| 3,776,284 | 12/1973 | Guyer et al. | 141/65 |
| 3,907,389 | 9/1975 | Cox et al. | 312/1 |
| 4,242,310 | 12/1980 | Greff et al. | 422/300 |
| 4,686,328 | 8/1987 | Ui et al. | 174/153 |
| 4,995,420 | 2/1991 | Wiggins | 137/360 |
| 5,017,197 | 5/1991 | McGuire et al. | 55/1 |
| 5,139,318 | 8/1992 | Broxup | 312/1 |
| 5,148,945 | 9/1992 | Geatz | 222/1 |
| 5,316,733 | 5/1994 | Rune et al. | 411/104 |
| 5,322,095 | 6/1994 | Bolz | 141/83 |
| 5,330,072 | 7/1994 | Ferri, Jr. et al. | 222/1 |
| 5,380,078 | 1/1995 | Baczkowski et al. | 312/1 |
| 5,417,346 | 5/1995 | Ferri, Jr. et al. | 222/61 |
| 5,460,439 | 10/1995 | Jennrich et al. | 312/1 |
| 5,465,766 | 11/1995 | Siegele et al. | 141/198 |
| 5,562,130 | 10/1996 | Peha et al. | 141/98 |

Primary Examiner—Jill Warden
Assistant Examiner—Saeed Chaudhry
Attorney, Agent, or Firm—J. Nevin Shaffer, Jr.; Shaffer & Culbertson, LLP

[57] ABSTRACT

A clean connection and sampling apparatus (10) and method for creating a controlled environment for the transfer of chemicals has an isolation means for providing an isolated area (14) capable of being cleaned. A first connection means (16) for connection to a supply of chemicals to be transferred is provided and a second connection means (18) for transferring the chemicals from the isolation means to a receiver for said chemicals is also provided. A sampling means is located within the isolation means for sampling the chemical prior to transfer to the receiver. A pass-through means (22) is provided for receiving a sample from within the isolation means and isolating the sample from the isolation means prior to transfer of the sample outside of the isolation means for analysis. A gas purge means (26) is provided and connected to the isolation means for purging the isolation means with gas, preferably an inert gas such as nitrogen, and for forcing the chemical from the chemical supply through the isolation means to the receiver. A spray means (28) is also provided within the isolation means for operation by means of accordion gloves attached to accordion glove ports (34) to prevent contamination of the interior of the isolation means while enabling manipulation of the interior parts, such as stop valve (17), sampler (20) and spray means (28). The spray means (28) is connected to a source of ultra-pure water for cleansing the interior prior to and subsequent to use along with the gas purge device (26). Additionally, a sump (36) and sump drain is provided for the removal of contaminated water as desired.

20 Claims, 4 Drawing Sheets

CLEAN CONNECTION AND SAMPLING APPARATUS AND METHOD

BACKGROUND OF THE INVENTION

This invention relates to an improved connection and sampling apparatus and method for transferring chemicals. In particular, this invention relates to the transfer of high purity peroxide from ISO tank trailers to fabrication plants through a clean connection and sampling device that detects contamination prior to transfer, prevents contamination during the transfer, and enables containment of contaminates and proper disposal of them should any occur.

The standard in the industry for the transfer of caustic chemicals for use in manufacturing processes is the connection of a hose to tank truck and to the input valve of the receiving manufacturing plant. Particularly, in the field of the fabrication of microchips, the requirements for cleanliness are exactingly high. The problem with the standard of delivery in the art today is that, in the process of making the connection to the delivery tank, connecting the delivery hoses themselves, and making a connection to the fabrication facility, opportunities exist for contamination of the high purity chemicals which are being delivered. A variety of patents have issued in various fields for the protection of the purity and cleanliness of materials as they are transferred from one environment to another. For example, the Jennrich, et al. Patent, U.S. Pat. No. 5,460,439 describes a sealed transfer system for use primarily in the medical environment for the transfer of pharmaceuticals from a "dirty" environment to a "clean" environment. A series of sealed doors and intermittent sterilization processes are used to ensure that a previously sterilized container of pharmaceuticals may be connected to the transfer port, the connection sterilized, the port opened and the material transferred without contaminating the clean environment.

Other patents have issued that are more directly related to the primary field of the invention such as the Ferri, Jr., et al. Patent, U.S. Pat. No. 5,417,346, which is directed to the field of transfer, storage and delivery of process chemicals. In particular, the invention concerns the delivery of ultra-high purity chemicals for use in a variety of industries such as the manufacture of semi-conductor wafers and similar products. The gist of this invention is the use of a vacuum system to draw chemicals through sealed conduits, thereby eliminating the need for pumps, which are sources of both maintenance problems and contamination in the system. The Ferri invention utilizes a vacuum to fill a remote vessel and then utilizes pressure to transfer the chemical in the filled vessel to the in-use station.

A drawback to the standard procedures utilized in the fabrication industry and disclosed in the art of which the Applicant is aware, is that although the ISO tank trailer is sterilized, the hoses are not. Additionally, the receiving end of the fabrication facility is generally exposed and capable of contamination. Also, a drawback to the systems known to the Applicant is that there is no method for making a clean contaminate free transfer after first verifying that the chemical itself is pure and uncontaminated. Thus, there is a need in the art for providing a clean connection and sampling apparatus for creating a controlled environment for the transfer of chemicals. It, therefore, is an object of this invention to provide an enclosed, improved, clean connection and sampling apparatus and method for creating a controlled environment for the transfer of chemicals which isolates the transfer area, keeps it contaminate free, is capable of cleaning after transfer and before, and which is capable of sampling the chemical to be transferred prior to transfer.

SHORT STATEMENT OF THE INVENTION

Accordingly, the clean connection and sampling apparatus for creating a controlled environment for the transfer of chemicals in the present invention includes an isolation means for providing an isolated area capable of being cleaned. A first connection means for connection to a supply of chemicals to be transferred is provided along with a second connection means for transferring the chemicals from the isolation means to a receiver for the chemicals. A sampling means is located within the isolation means for sampling the chemical prior to transfer to the receiver. Also, located within the isolation means is a pass-through device for receiving a sample from within the isolation means and then isolating the sample from the isolation means prior to transfer of the sample outside of the isolation means for analysis. Additionally, the present invention includes a gas purge means connected to the isolation means for purging the isolation means with gas, in particular inert gas such as nitrogen, prior to the transfer of any chemicals. The gas purge means is also connected to the chemical supply for use in forcing the chemical to the receiver. Additionally, a spray means is located within the isolation means for manually, physically cleaning the inside of the isolation means prior to and/or subsequent to use. In a preferred embodiment, the isolation means further includes accordion glove ports for handling sample holders and operating the isolation means without introducing contaminates therein. Still further, in a preferred embodiment, the first connection means includes an iris connection port that fully encompasses and seals a connecting hose from the receiver and thereby isolates the hose within the isolation means so that it may be cleaned prior to and subsequent to transfer. Still further, in a preferred embodiment, the sampling means includes a sampler with two needles, one for accepting the sample from the chemical as it enters the isolation means and one for providing a vent within the isolation means. Yet still further, in another embodiment of the invention, the spray means includes a sump for collecting contaminates and for draining the contaminates outside the isolation means when appropriate. Still further, in a preferred embodiment, the gas purge means of the invention includes a three way connection port alternately connected to a source of purging gas, the supply of chemicals and the isolation means so that as necessary, the user can clean, evacuate or isolate the isolation means from the gas purging means and/or force chemicals through the isolation means as desired.

BRIEF DESCRIPTION OF THE DRAWINGS

Other objects, features, and advantages of the present invention will become more fully apparent from the following detailed description of the preferred embodiment, the appended claims, and the accompanying drawings in which:

DETAILED DESCRIPTION OF THE PREFERRED EMBODIMENT

Figure 1:
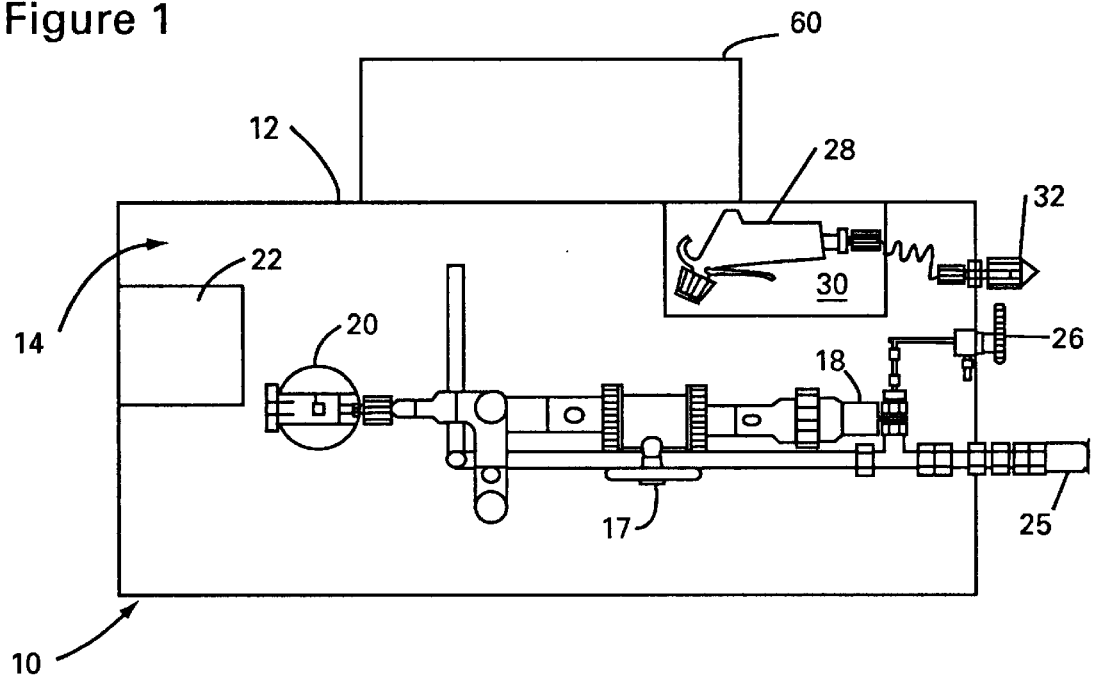
FIG. 1 is a top view of a preferred embodiment of the clean connection and sampling system of the present invention showing the interior configuration of the isolation means.

The preferred embodiment of the present invention is illustrated by way of example in FIGS. 1 through 8. With specific reference to FIGS. 1 and 2, a clean connection and sampling apparatus 10 includes a frame 12 which is in the form of a rectangular box. Frame 12 creates an isolated area 14 capable of being cleaned. A first connection 16 is provided for connection to a supply of chemicals to be transferred to and through clean connection and sampling apparatus 10. A second connection 18 is provided for transferring the chemicals from the isolated area 14 within frame 12 to a receiver for the chemicals (not shown) such as a fabrication plant or some other industrial facility. A sampler 20 is located within the isolated area 14 formed by frame 12 so as to enable sampling of the chemical prior to transfer to the receiver. As more clearly illustrated in FIGS. 5 and 6, a pass-through 22 is provided within isolated area 14 formed by frame 12 so as to allow a sample to be taken by means of sampler 20 of the chemical prior to transfer to the receiver. The pass-through 22 creates an isolated area 24 within which the sample can be placed prior to transfer outside of isolated area 14 for analysis.

A gas purge 25 is connected to isolated area purge connection 26 for purging the isolated area 14 with gas and is connected through a gas purge connection 27 to the supply of chemicals as will be described more fully hereafter. Additionally, a spray gun 28 is located in isolated area 14 supported by spray gun port tray 30. Spray gun 28 has an external connection 32 to which an ultra-pure water source (not shown) is attached.

Figure 2:
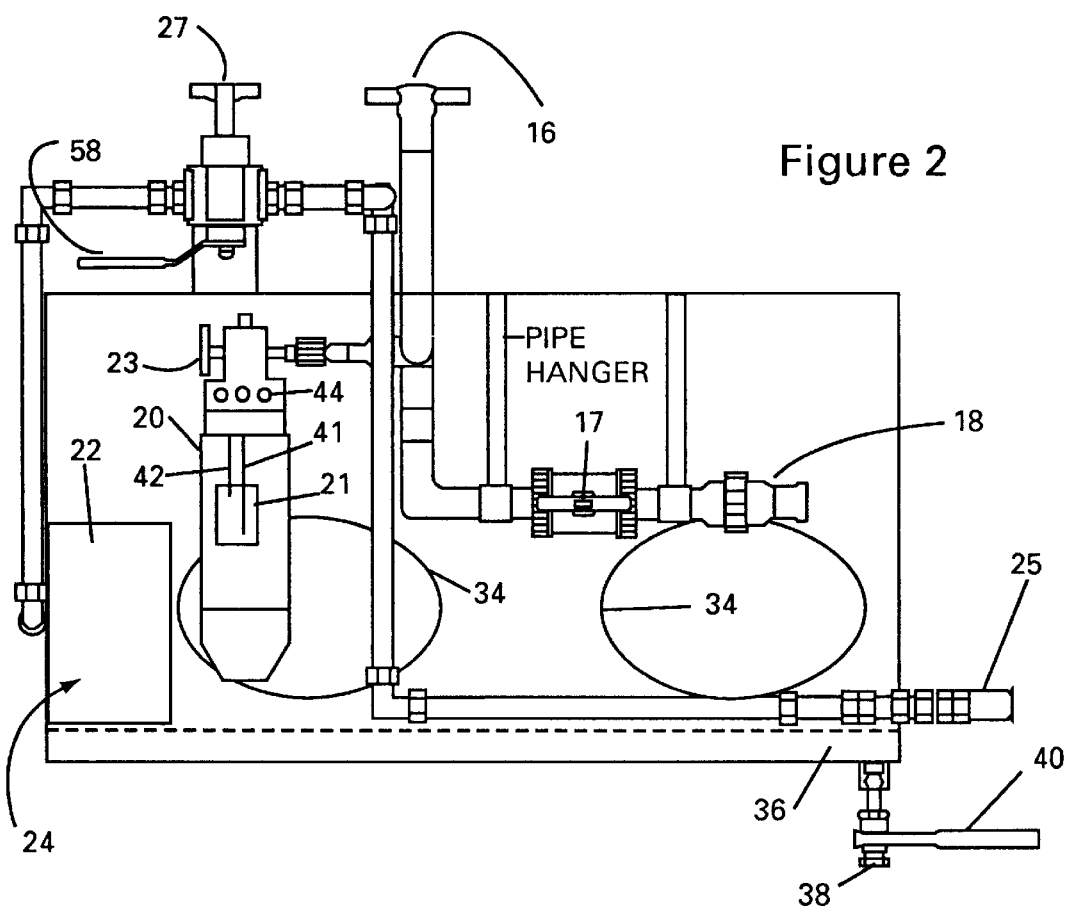
FIG. 2 is a front view of FIG. 1.

Referring to FIG. 2, glove ports 34 are shown in frame 12 to which accordion gloves, known in the art and not shown or disclosed further hereafter, are attached so that isolated area 14 may be penetrated and valves and the like manipulated by the user of the glove ports without contaminating isolated area 14. Sump 36 is connectable to a sump pump, known in the art and not disclosed hereafter, by means of connection 38 and operable by means of operating handle 40 so that after use of spray gun 28, contaminates and a mixture of ultra-pure water used to clean the interior isolated area 14 may be removed from within frame 12.

Sampler 20 includes sample holder 21 and two needles 41 and 42, one needle 41 for drawing a sample of chemical to be analyzed and one needle 42 for venting at vent 44 within isolated area 14.

Figure 3:
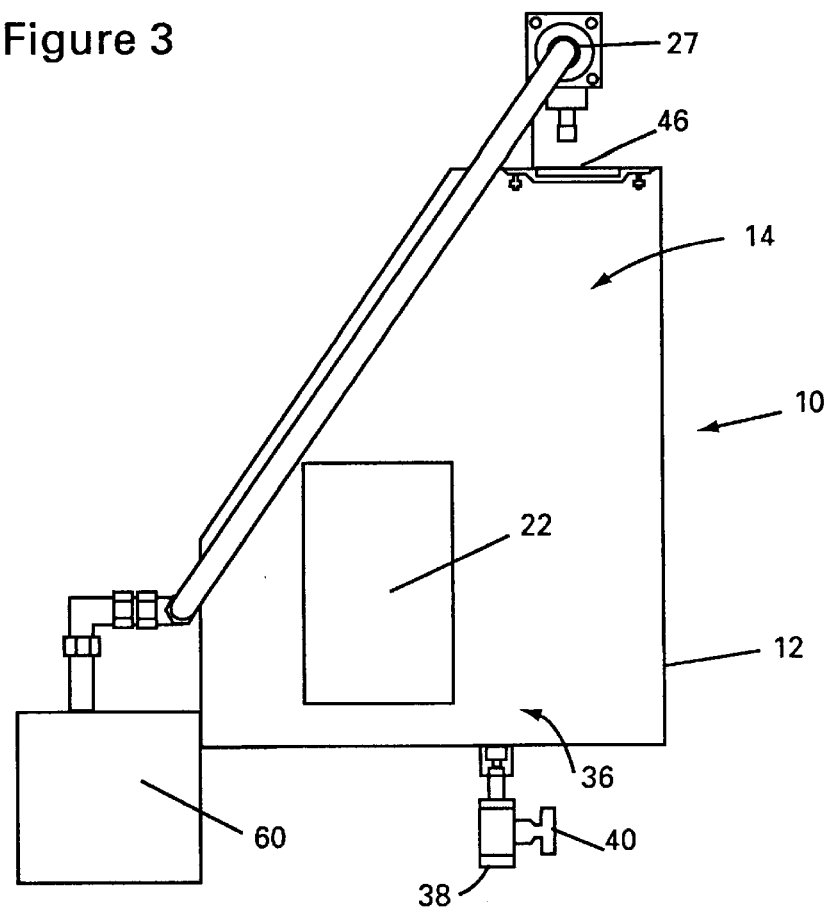
FIG. 3 is a left side view of FIG. 1.
Figure 4:
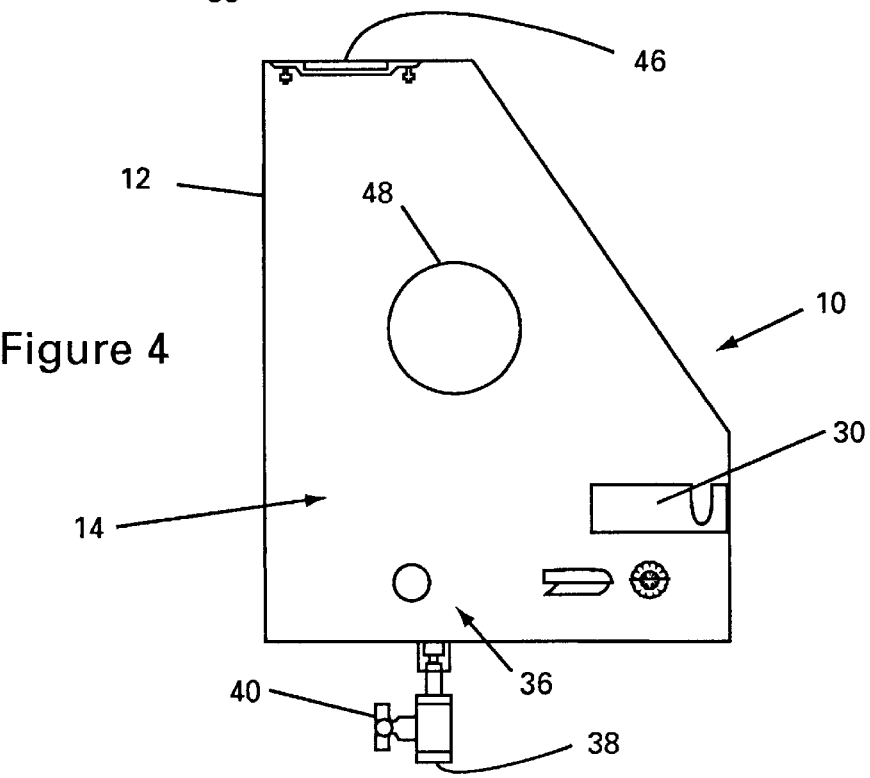
FIG. 4 is a right side view of FIG. 1.

Referring now to FIGS. 3 and 4, the clean connection and sampling apparatus 10 of the present invention is shown further illustrating some of the internal and external elements of the invention, including skylights 46, pass-through 22 and iris port 48. Iris port 48, known in the art and not disclosed more fully hereafter, constricts around the hose, not shown, from the receiver so as to form a seal around the hose prior to transfer of any chemicals. The hose from the receiver will be connected to second connection 18 after passing through iris port 48. Prior to connection of the hose to second connection 18, the hose may be cleaned, after being secured within iris port 48, by means of spray gun 28 so that the connecting end of the hose is cleaned prior to attachment to second connection 18. This is a large source of contamination in prior art devices. The ability to create a cleansed, non-contaminated connector with an everyday hose within isolated area 14 is a large advantage of the present invention.

Figure 5:
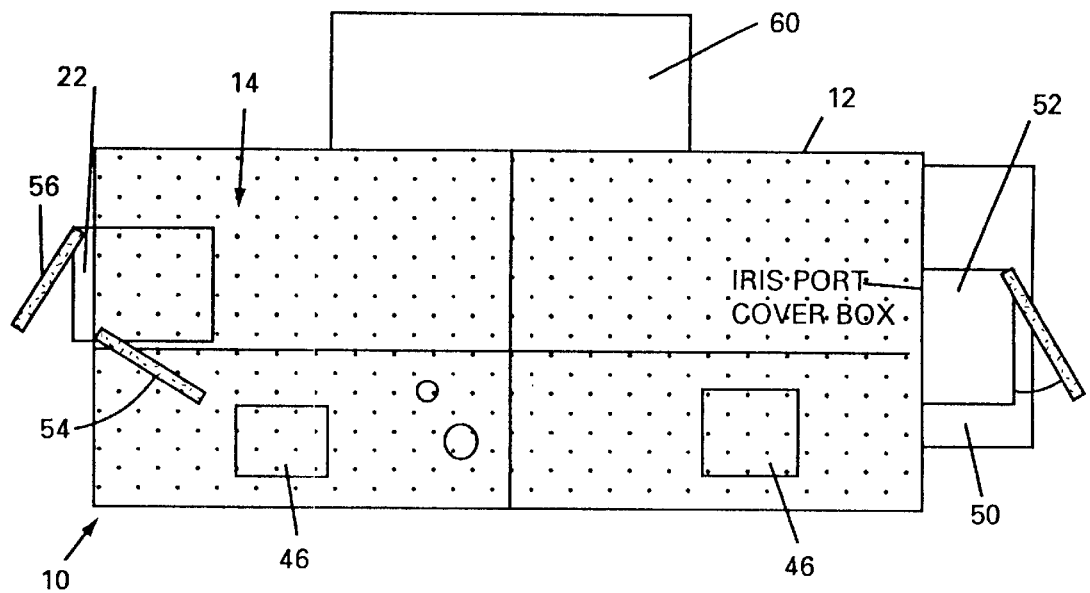
FIG. 5 is a top view of the invention in FIG. 1 showing in dotted lines the exterior of the top and associated interior and exterior elements.
Figure 6:
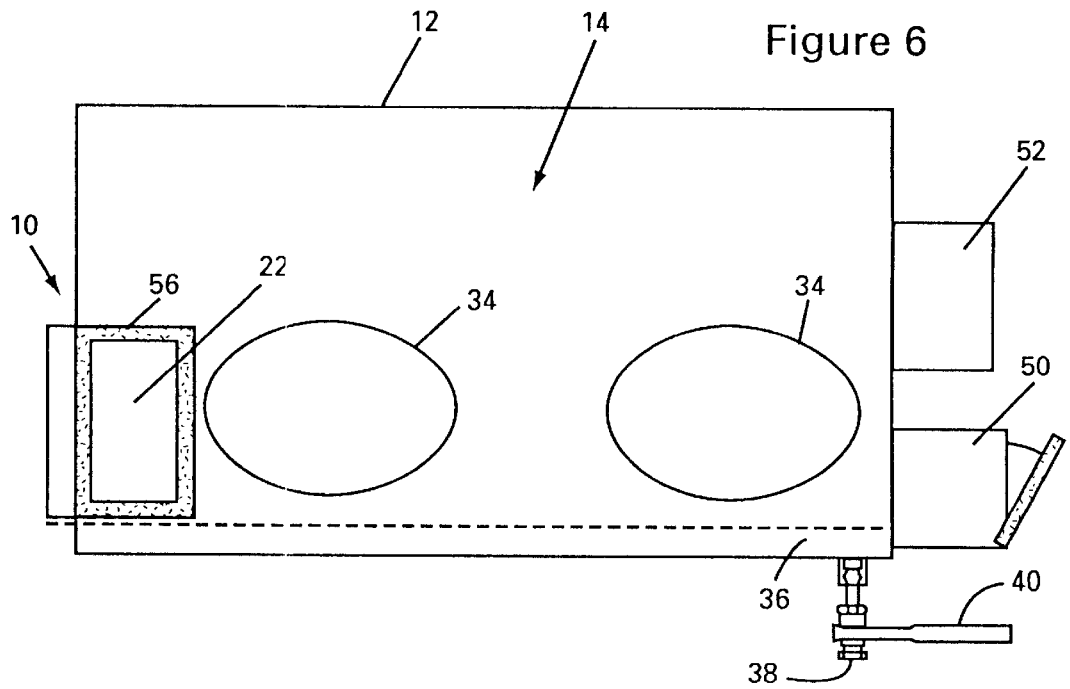
FIG. 6 is a front view of FIG. 5.
Figure 7:
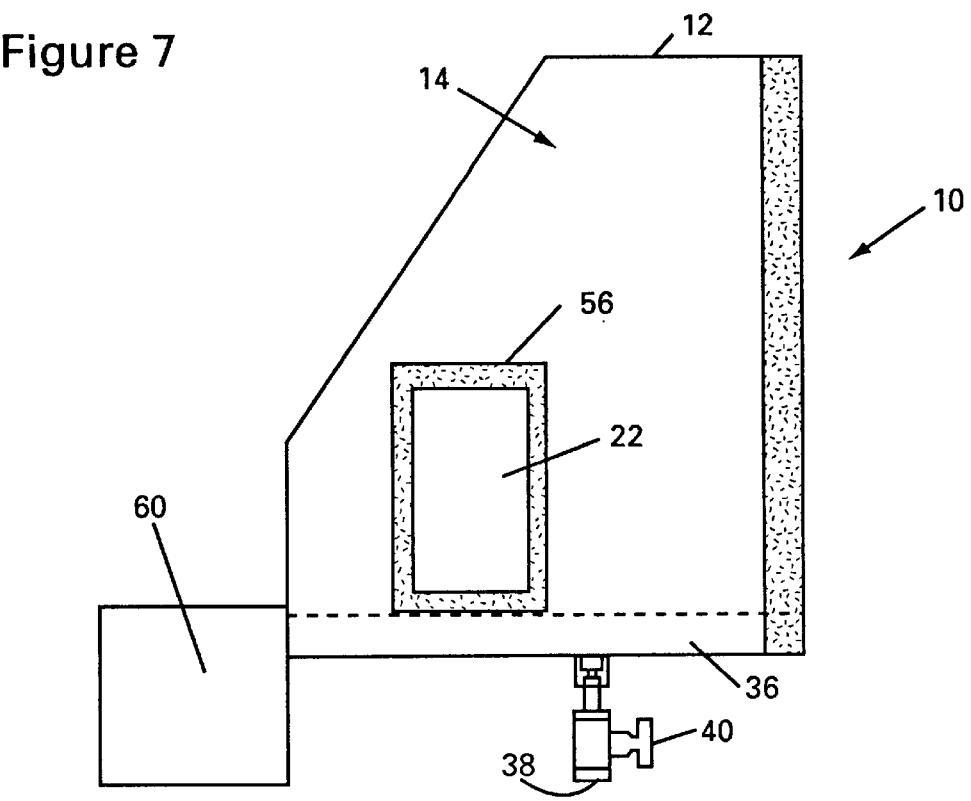
FIG. 7 is a left side view of FIG. 5.
Figure 8:
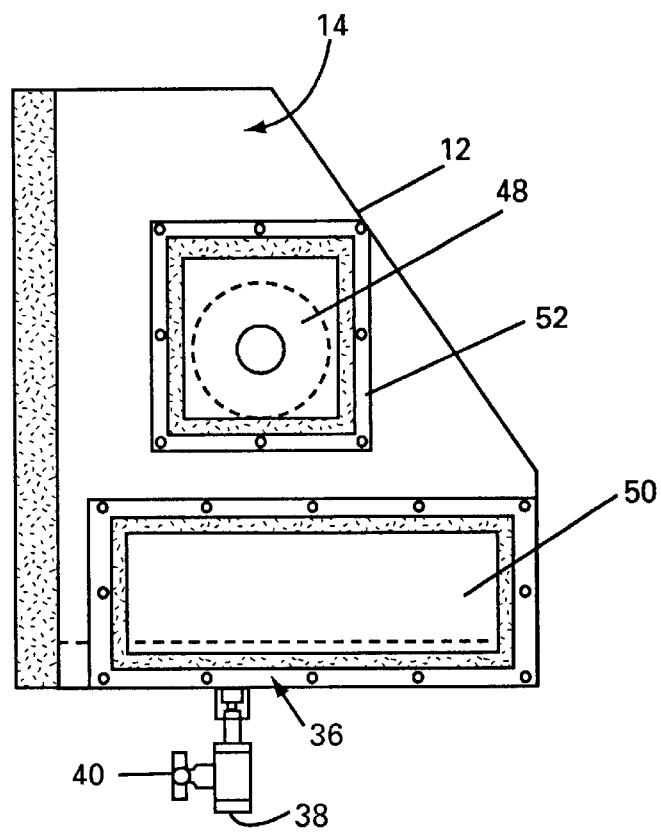
FIG. 8 is a right side view of FIG. 5.

Referring now to FIGS. 5 and 6, additional elements connected to frame 12 of clean connection and sampling apparatus 10 are more clearly illustrated. Skylights 46 are shown in FIG. 5, along with nitrogen source connection and ultra-pure water source connection cover box 50 within which are located a nitrogen gas source connection 25 and an ultra-pure water source connection 32. Nitrogen, or any other gas, source and ultra-pure water source (not shown) are attached prior to operation. Additionally, iris port 48 has iris port cover box 52 attached to frame 12 so as to protect iris port 48 when not in use. Also illustrated is pass-through 22 showing interior pass-through door 54 and exterior pass-through door 56. Referring to FIGS. 7 and 8, left and right side views are illustrated showing iris port cover box 52 and nitrogen source and ultra-pure water source cover box 50 in position on frame 12, as well as showing exterior pass-through door 56 in place on pass-through 22 connected to frame 12.

In operation, in a preferred embodiment, clean connection and sampling apparatus 10 is hard connected by means of first connection hose 16 to an ISO tank trailer containing high purity chemicals, such as peroxide, for use in wafer fabrication facilities. Next, gas purge connection 27 is hard connected to the ISO tank trailer. Upon arrival at the facility, a hose from the facility is connected to clean connection and sampling apparatus 10 through iris port 48 at second connection 18. Iris port 48 operating as is known in the art completes a seal around the transferring hose ensuring that the interior isolated area 14 formed by frame 12 is sealed to the outside environment. Once sealed, the hose can be cleaned by means of spray gun 28 and the contaminated fluid removed from isolated area 14 by means of sump 36 and, associated sump pump. Prior to transfer, nitrogen source is activated and isolated area 14 and associated transferring tubes and the like are purged by this purging gas source as follows.

In operation, an inert gas source such as nitrogen is connected to gas purge 25. When activated, gas is allowed to proceed to isolated area purge connection 26. Upon opening of isolated area purge connection 26, inert gas, again, preferably nitrogen, is allowed to purge the entire isolated area 14 with gas. Once that is completed, and isolated area 14 is ready for transferring the chemical, gas purge connection 27 is opened so that nitrogen gas flows through gas purge 25 lines through gas purge connection 27 and into the ISO tank trailer holding the chemical. By way of this operation, then, gas is utilized to push the chemical from the tank truck so that the chemical flows from the tank truck through first connection 16 to stop valve 17. At that point, the chemical is ready for testing at sampler 20. Sample valve 23 is operated allowing the chemical to enter through needle 41 while venting through needle 42 thereby allowing sample to be collected in sample holder 21. At that point, sample valve 23 is shut off, sample holder 21 is passed through pass-through 22 and analyzed. If the analysis is positive, stop valve 17 is operated so as to allow chemical to pass by stop valve 17 through second connection 18 into the hose sealed within iris port 48 and to the receiver fabrication facility.

When nitrogen source is engaged, three way valve 58 is placed in a closed position so that nitrogen, in fact, is available at isolated purge connection 26 to purge isolated area 14. At that point, a second connection 18 is made with the receiving facility. The hose connection, at second connection 18, has previously been cleaned by means of spray gun 28 as necessary and clamped in position by iris port 48 and sealed thereby. Once the connection is made with the facility, three way valve 58 is moved to the position to allow nitrogen to flow from it through gas purge connection 27 into the ISO tank trailer thereby forcing the high purity chemical out of the ISO tank trailer past first connection 16. Stop valve 17 is closed at this point preventing the transfer of the chemical out of clean connection and sampling apparatus 10. Once contained within isolated area 14, the chemical is directed to sampler 20 where sampler 20 is utilized to collect a sample of the chemical prior to transfer of the chemical to the receiving facility. Sample holder 21, positioned within sampler 20, receives needles 41 and 42 and as chemical is introduced into sample holder 21, needle 42 allows the sample holder to vent through vent 44, thereby allowing the chemical to enter the sample holder 21. Once a sample has been taken, the sample is then placed, by means of glove ports 34 and associated accordion gloves for handling the sample holder 21, within pass through 22 and interior pass through door 54 is shut. Once interior pass through door 54 is closed, sample holder 21 may be removed through exterior pass through door 56 and analyzed. Upon completion of the analysis indicating acceptable purity, the user operates stop valve 17 to place it in the open position. As a result, then, the chemical is pushed by means of the purging gas from the ISO tank trailer, through the clean connection sample apparatus 10 to the receiving facility.

By way of frame 12 creating isolated area 14, should any leak occur, the leak is contained within the isolated area 14 and may be removed when and if necessary through sump 36. Once the chemical transfer is completed, second connection 18 is disconnected and the hose is removed from iris port 48 and iris port cover box 52 is closed. Just prior to removal of the hose, the hose may be again cleaned if necessary by means of spray gun 28. At this point, the interior isolated area 14 may be completely cleaned by means of spray gun 28 utilizing ultra-pure water provided from the outside of frame 12 through connection 32. Contaminated water and the like may be removed again, through sump 36 as previously described. At this point, gas purge 26 may be utilized to purge the system again with an inert gas such as nitrogen in a preferred embodiment and clean connection and sampling apparatus 10 secured against the introduction of contaminates thereafter.

Once the transfer of the chemical is completed, three way valve 58 is open to the air so that the purging gas now contained within the ISO tank trailer can be released from the ISO tank trailer and passed through gas and air filter 60. Isolated area 14 is also capable of being vented through gas and air filter 60 so that any resultant chemical and chemical reaction are precluded from harming the interior of frame 12. By means of gas and air filter 60, the interior of ISO tank trailer is also kept contaminate free and ready for receipt of additional chemical supplies at turn around.

By way of the present invention, an isolated area 14 is created so that a clean environment for the connection of distribution piping and the taking of the samples exists. Additionally, frame 12 creates in isolated area 14 an ability to contain and control any spilled chemical that might result in the transfer. Additionally, frame 12 includes venting and air intakes 60 so as to protect the isolated area 14 and the chemical tank truck from overexposure to caustic chemicals should they exist. As a result, clean connection and sampling apparatus 10 solves the problem of contamination of high purity chemicals during transfer and assists in maintaining a contamination free environment after transfer in both the isolated area 14 and tank truck.

Frame 12 may be constructed of any material known in the art that is resistant to chemical corrosion such as certain clear plastics, glass, metals and the like. Additionally, a removable shield of non-breakable metal, such as stainless steel or the like is utilized in a preferred embodiment to shield clean connection and sampling apparatus 10 as it is transported along with ISO tank truck from place to place. Again, it is envisioned in a preferred embodiment that clean connection and sampling apparatus 10 is hard connected to the ISO tank truck as previously described, thereby greatly speeding up the process of providing a clean environment for the transfer of chemicals. Alternately, the clean connection and sampling apparatus 10 of the present invention may be transported from site to site and chemical delivery vehicle to chemical delivery vehicle should that be preferred. While the preferred embodiment is with use with high purity peroxide, the clean connection and sampling apparatus 10 of the present invention may be used in any situation where high purity chemicals need to be transferred in an isolated safe spillage containment manner.

While the present invention has been disclosed in connection with the preferred embodiment thereof, it should be understood that there may be other embodiments which fall within the spirit and scope of the invention as defined by the following claims.

We claim:

1. A clean connection and sampling apparatus for creating a controlled environment for the transfer of chemicals comprising:

(a) an isolation means for providing an isolated area capable of being cleaned;
   (b) a first connection means for connection to a supply of chemicals to be transferred;
   (c) a second connection means for transferring said chemicals from said isolation means to a receiver for said chemicals;
   (d) a sampling means within said isolation means for sampling said chemical prior to transfer to said receiver;
   (e) a pass through means for receiving a sample from said isolation means and isolating said sample from said isolation means prior to transfer outside said isolation means;
   (f) a gas purge means connected to said isolation means for purging said isolation means with gas and forcing said chemicals from said supply of chemicals; and
   (g) a spray means within said isolation means for cleaning the inside of said isolation means.

2. The apparatus of claim 1 wherein said isolation means further comprises accordion glove ports for handling sample holders and operating the isolation means without introducing contaminates therein.

3. The apparatus of claim 1 wherein said isolation means further comprises a transparent, break resistant enclosure with a moveable break-proof cover for covering said isolation means when said isolation means is not in use.

4. The apparatus of claim 1 further comprising removably attachable connections for connecting said isolation means to chemical tank trailers.

5. The apparatus of claim 1 wherein said first connection means further comprises an iris connection port so as to fully encompass and seal a connecting hose to said receiver.

6. The apparatus of claim 1 wherein said supply of chemicals is high purity peroxide.

7. The apparatus of claim 1 wherein said sampling means further comprises a sampler with two needles, one for depositing a sample from said chemical as it enters said isolation means and one for providing a vent within said isolation means.

8. The apparatus of claim 1 wherein said spray means further comprises a sump for collecting contaminates created and for draining said contaminates outside said isolation means.

9. The apparatus of claim 1 wherein said gas purge means further comprises a three way connection port alternately connected to a source of purging gas, the supply of chemicals and the isolation means.

10. The apparatus of claim 9 wherein said source of purging gas is nitrogen.

11. In microchip fabrication facilities wherein high purity peroxide is transferred from an ISO tank trailer to the fabrication facility, a clean connection and sampling apparatus comprising:

(a) an isolation means for providing an isolated area capable of being cleaned;

(b) an iris connection port for fully encompassing and sealing a connecting hose to the fabrication facility;

(c) a connection means for transferring said high purity peroxide from said ISO tank trailer to said isolation means;

(d) a sampling means within said isolation means for sampling said high purity peroxide prior to transfer to said receiver means;

(e) a pass through means for receiving a sample from said isolation means and isolating said sample from said isolation means prior to transfer outside said isolation means;

(f) a gas purge means connected to said isolation means for purging said isolation means with inert gas and for forcing said chemicals from said ISO tank trailer;

(g) a spray means within said isolation means for cleaning the inside of said isolation means; and (h) accordion glove ports for handling sampling holders and operating devices within the isolation means without introducing contaminates therein.

12. A clean connection and sampling method for creating a controlled environment for the transfer of chemicals comprising the steps of:

(a) constructing an isolation means for providing an isolated area capable of being cleaned;

(b) providing a first connection means within said isolation means for connecting said isolation means to a supply of chemicals outside of said isolation means;

(c) providing a second connection means within said isolation means for transferring said chemicals from within said isolation means to a receiver for said chemicals located outside of said isolation means;

(d) providing a sampling means within said isolation means for sampling said chemical prior to transfer to said receiver means;

(e) providing a pass through means for receiving a sample from said isolation means and isolating said sample from said isolation means prior to transfer of said sample outside of said isolation means;

(f) providing a gas purge means connected to said isolation means for purging said isolation means with inert gas and for forcing said chemical from said supply of chemicals;

(g) providing a spray means within said isolation means for cleaning the inside of said isolation means;

(h) purging the isolation means with said inert gas so as to remove contaminates;

(i) transferring chemicals, using said inert gas, from the outside of said isolation means to the interior of said isolation means;

(j) sampling the chemical;

(k) continuing the transfer of chemicals from within said isolation means to the receiver for said chemicals; and (l) cleaning the interior of said isolation means with said spray means.

13. The method of claim 12 further comprising the step of providing accordion glove ports for handling sampling holders and operating devices within the isolation means without introducing contaminates therein.

14. The method of claim 12 wherein the step of providing said isolation means further comprises the step of constructing said isolation means of transparent, break resistant material and connecting a moveable break-proof cover to said isolation means for covering said isolation means when said isolation means is not in use.

15. The method of claim 12 further comprising the step of removably attaching said isolation connection means to a chemical tank trailer.

16. The method of claim 12 wherein the step of providing a connection means to a receiver of said chemicals further comprises the step of providing an iris connection port so as to fully encompass and seal a connecting hose to said receiver.

17. The method of claim 12 wherein the step of providing a sampling means further comprises the step of providing a sampler with two needles, one for depositing a sample from said chemical as it enters said isolation means and one for providing a vent within said isolation means.

18. The method of claim 12 wherein the step of providing a spray means further comprises the step of providing a sump, for collecting contaminates and for draining said contaminates outside of said isolation means.

19. The method of claim 12 wherein the step of providing a gas purge means further comprises the step of providing a three way connection port alternately connected to a source of purging gas, the supply of chemicals and the isolation means.

20. The method of claim 12 wherein the step of connecting the gas purge means to a source of purging gas further comprises the step of using nitrogen as the purging gas.

* * * * *